United States Patent [19]

Chan

[11] Patent Number: 5,168,588
[45] Date of Patent: Dec. 8, 1992

[54] MASSAGING MATTRESS

[76] Inventor: Hoi Chau Chan, 8/F, Blk. 3 Flat A, 218-240, Castle Peak Road, New Territories, Hong Kong, Hong Kong

[21] Appl. No.: 734,463

[22] Filed: Jul. 23, 1991

[30] Foreign Application Priority Data

Aug. 4, 1990 [CN] China .............................. 90217459.2

[51] Int. Cl.$^5$ ............................................. A47C 27/00
[52] U.S. Cl. .......................................... 5/448; 5/468; 5/911
[58] Field of Search ................... 5/446, 447, 448, 461, 5/468, 481; 600/9, 15

[56] References Cited

U.S. PATENT DOCUMENTS

| | | | |
|---|---|---|---|
| 3,829,917 | 8/1974 | De Laittre et al. | 5/436 |
| 4,330,892 | 5/1982 | Fukushima | 5/437 |
| 4,509,219 | 4/1985 | Yagi | 5/448 X |
| 4,903,356 | 2/1990 | Morisaki | 5/448 X |
| 4,924,542 | 5/1990 | Yamaguchi | 5/448 X |
| 5,035,017 | 7/1991 | Komuro | 5/448 X |
| 5,105,490 | 4/1992 | Shok | 5/468 X |

FOREIGN PATENT DOCUMENTS

| | | |
|---|---|---|
| 2032055U | 2/1989 | China . |
| 2044145U | 9/1989 | China . |
| 2045599U | 10/1989 | China . |
| 2323851 | 11/1974 | Fed. Rep. of Germany .......... 5/431 |

OTHER PUBLICATIONS

English translation of Chinese Patent No. CN 2044145U. (Abstract and claim 1 only).
English translation of Chinese Patent No. CN 2045599U. (Abstract and claim 1 only).
English translation of Chinese Patent No. CN 2032055U. (Abstract and claim 1 only).

Primary Examiner—Michael F. Trettel
Attorney, Agent, or Firm—Merchant, Gould, Smith, Edell, Welter & Schmidt

[57] ABSTRACT

This invention relates to a massaging mattress, comprising an elastic stuffing and a compound covering, and an array between said stuffing and covering, composed of wooden beads alternating with magnets, said array being connected with ropes to form a net. In use, the beads and magnets will roll slightly, producing a feeling of being massaged by a thousand hands. The mattress according to this invention can not only relieve back pain, etc., but also promote blood circulation. It is suitable for use in both winter and summer, and is convenient for store and transport.

20 Claims, 2 Drawing Sheets

MASSAGING MATTRESS

BACKGROUND OF THE INVENTION

The invention relates to a personal and domestic article, particularly to a mattress or pillow having a massaging function.

Prior art mattresses are made up of elastic stuffings like fibre or sponge made from coconut fibre, coiled springs and compound coverings. Although this kind of mattress is comfortable for sleeping, yet it has no therapeutic function; nor is it suitable for use in hot summer. Chinese Patent CN203205U disclosed a kind of magneto-therapeutic spring mattress, in which there are provided some magneto-therapeutic lumps with field intensities varying according to the different degrees of magnetic endurance in different parts of the human body. But the therapeutic function of that invention is only good for the neck and the waist, and there is no ventilation design, thus making it unsuitable for use in hot summer. Another Chinese Patent CN2045599U disclosed a mattress usable in both winter and summer. The aforementioned two kinds of mattresses are either not suitable for summer use, or have no magnetic massotherapeutic effects. Moreover, their structures are too complicated.

OBJECTS OF INVENTION

The primary object of the present invention is to overcome the deficiencies in the afore-mentioned prior art, to provide a kind of mattress and pillow having not only a magneto-therapeutic function, but also massotherapeutic effects, and with an appropriate ventilation provided, so as to be also suitable for use in summer.

Another object of this invention is to provide a mattress having therapeutic effects, which is easy to sore and transport and is simple in structure with a low manufacturing cost.

Another object of the present invention can be attained with a kind of massaging mattress, comprising an elastic stuffing and a compound covering, between which is arranged an array composed of wooden beads alternating with magnets, said array being connected by ropes to form a layer of net, which in tun is stuck onto said elastic stuffing by a certain kind of glue.

BRIEF DESCRIPTION OF DRAWINGS

The above-mentioned objects as well as advantages of the present invention will become clear by the following description of preferred embodiments of the present invention with reference to the accompanying drawings, wherein.

DESCRIPTION OF INVENTION

Figure 1:
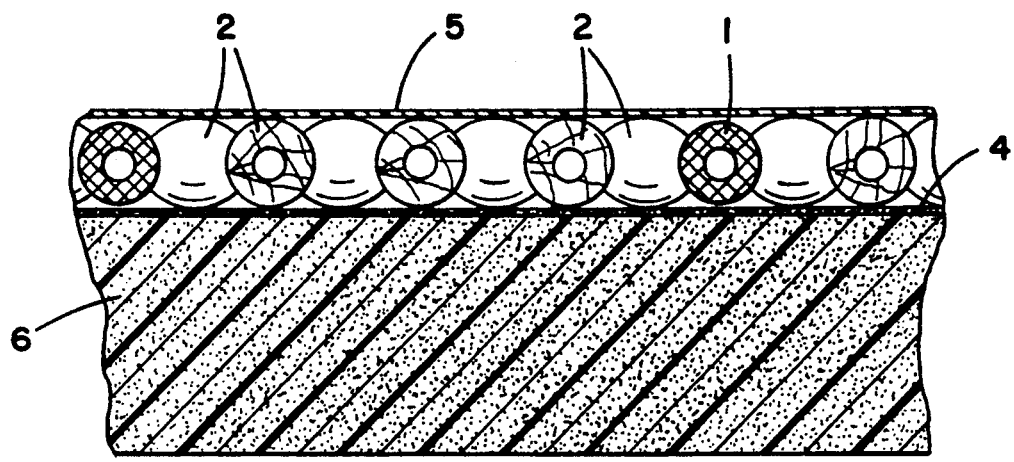
FIG. 1 is a sectional view of a massaging mattress showing the first embodiment of the present invention.
Figure 2:
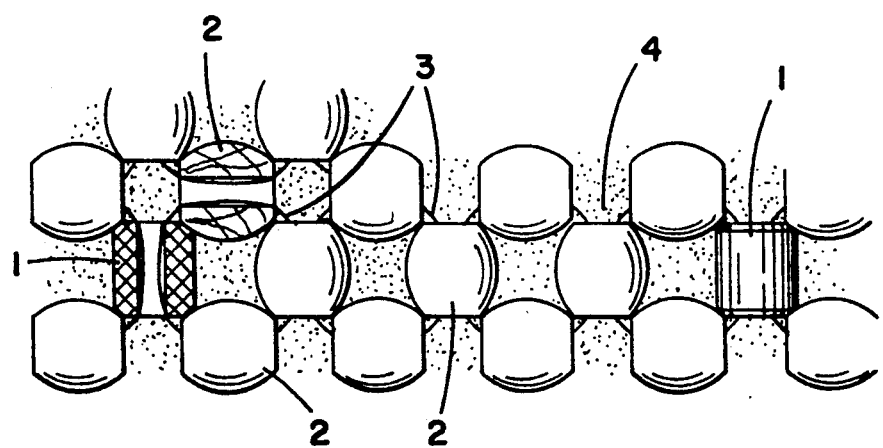
FIG. 2 is a plan view of the array composed of wooden beads alternating with magnets, for the 1st embodiment of the invention.

Referring to FIGS. 1 and 2, the massaging mattress of the present invention comprises an elastic stuffing 6 and a compound covering 5, with an array, arranged between them, composed of wooden beads 2 alternating with magnets 1, said beads 2 and magnets 1 being connected by ropes 3 to form a net, which in turn is stuck onto said elastic stuffing 6 by a certain kind of glue 4.

Figure 3:
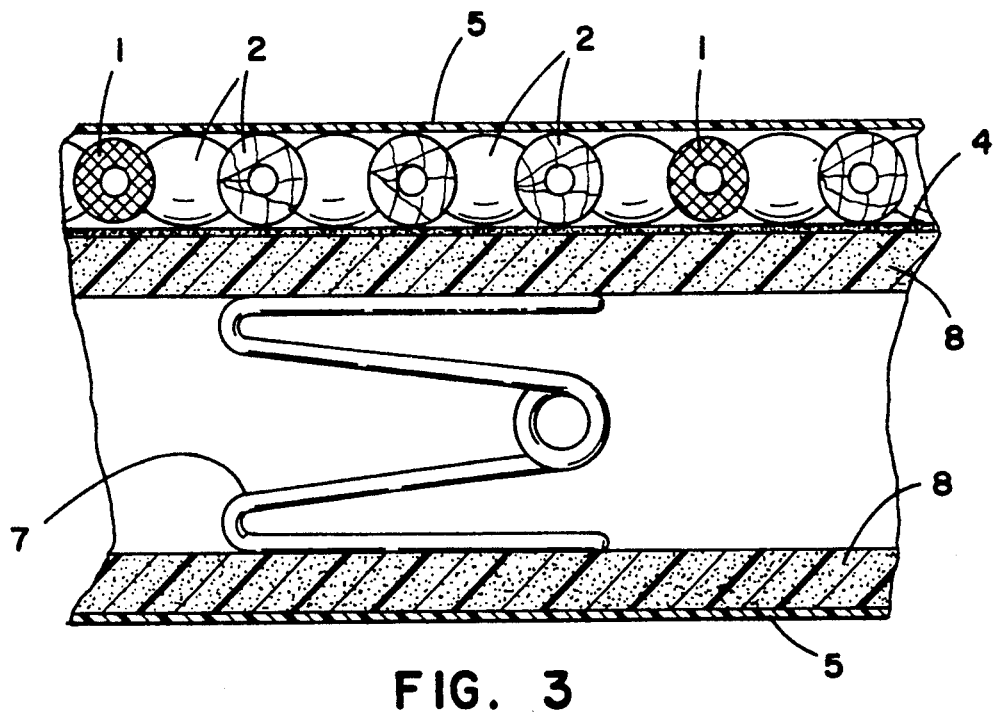
FIG. 3 is a view, similar to FIG. 1, of a second embodiment of the invention, in which the traditional coiled springs and foam plastics are adopted instead of the elastic stuffing.

Referring to FIG. 3, the elastic stuffing 6 can be made of sponge or foam plastics 8 as a whole, or of coiled springs 7 between two layers of foam plastics 8, as is traditional.

FIG. 4 shows a wooden bead, which in appearance looks like a truncated ellipsoid having two ends forming two parallel circular planes, with its maximum circular cross-sectional diameter disposed proximate its midportion being the same as its height which is a distance between its two ends (both about 16 mm). Provided through the center of each of said beads is an axial penetrating hole. Beads used in the mattress according to this invention can be made of such hard wood, as maple, mulberry or ash grown in the North-East of China.

FIG. 5 shows a magnet which is cylindrical in shape, with its diameter close to the height (both about 16 mm). There is also provided an axial penetrating hole through the centre of said magnet. Magnets used for the mattress according to the present invention can be made of permanent magnet of ferrite, alnico, or permanent magnet of rare-earths-cobalt or other processable permanent magnet. The surface field intensity of said magnets should range from 500 to 2000 Gauss.

Referring back to FIGS. 2 and 3, the rope 3 used to connect said beads and magnets can be made of nylon, polyamide fibre, waxed cotton thread or silk thread, and the glue 4 can be the kind of glue generally used for indoor decoration.

Figure 6:
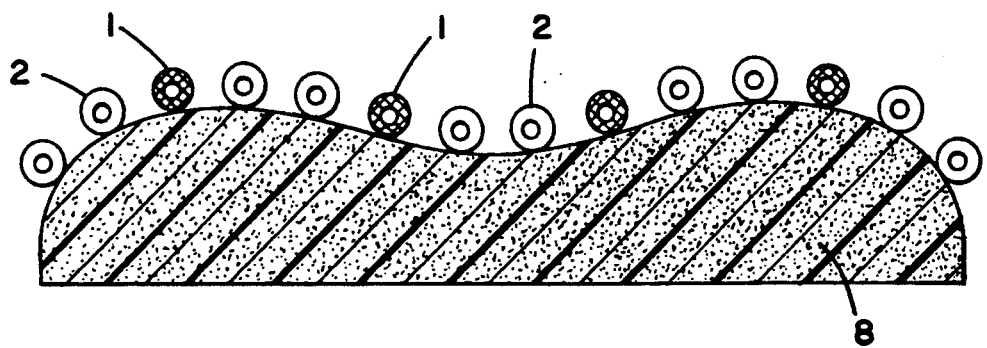
FIG. 6 is a view, similar to FIG. 1, of a third embodiment of the invention, comprising a pillow which has a waved surface.

When the structure according to this invention is applied to a pillow, the latter may be made to have a waved surface, and only two wooden beads 2 should be arranged between each two magnets 1, as is illustrated in FIG. 6.

With the structure according to this invention applied to a mattress, the array composed of wooden beads 2 and magnets 1, usually arranged near the upper surface of the mattress, could be of such an arrangement that there are provided three or five wooden beads between each two magnets, making the distance between each two magnets to be about 7 to 12 centimeters. The magnets in turn are strung together along with said wooden beads by ropes, to form a large net, of which the dimensions are matchable with the size of the mattress. Such a mattress can bear a weight of 600 kg without the net structure getting loose. Now coming to the beads, as each bead possesses a curved side surface, a certain amount of air is held between the beads, and when the mattress is pressed or slightly moved, the air will flow between the crevices formed in there and the beads and magnets will also roll slightly, thus producing a feeling as though the one lying thereon were being massaged by a thousand hands.

Besides this massotherapy function, the magnetic field produced by the magnets is also good for relieving a waist pain or back sore and promoting the blood circulation and metabolism, so as to relax the weary muscles.

Lastly, since the wooden beads and magnets have a waved convex surface to enable air flow, the mattress according to this invention is also suitable for use in hot summer, and produces an additional curing effect over rheumatism and skin diseases.

Compared with various mattresses of renowned brands available on the market, the massaging mattress according to this invention has the following advantages. In the first place, it is at once an article for daily use as well as for medical treatment; secondly, it can be used not only in winter and autumn and spring, but also in summer, particularly in places where there is no air-conditioning provided; thirdly, it can be rolled into a bundle and tied up, or spread on an uneven surface, without damaging the structure of disabling the aforementioned functions, and is therefore convenient for store or transport; it is light in weight, almost by ¼ lighter than similar products of renowned brands, and is therefore suitable for travelling purposes; finally, with a simple manufacturing process and simple structure, its manufacturing cost is only about ⅔ that of other produces of renowned brands.

Use of this mattress according to this invention by individuals including medical personnel has shown that it not only makes sleeping comfortable so that you get energetic after sleeping, but also lowers the blood pressure, relieves pains of various kinds, diminishes inflammation, calms the nerve system, cures rheumatism, and builds up body health.

What is claimed is:

1. A massaging mattress, comprising an elastic stuffing (6) and a compound covering (5), said mattress being provided between said elastic stuffing (6) and said compound covering (5) with an array including wooden beads (2) alternating with magnets (1), wherein said magnets (1) and said beads (2) are interconnected by flexible members so as to form a net, said magnets and said beads being provided with through holes penetrating the center of said beads and said magnets, said flexible members being received in said through holes, the through holes of said beads and said magnets in adjacent rows being orientated at approximately 90 degrees relative to each other.

2. A massaging mattress, as claimed in claim 1, wherein said beads (2) and said magnets (1) forming said array are connected by ropes (3), to form said net, said net being stuck onto said elastic stuffing (6) by a glue (4).

3. A massaging mattress, as claimed in claim 2, wherein said ropes (3) can be of nylon, polyamide fibre, waxed cotton thread or silk thread, and said glue (4) can be any kind of glue, generally used for indoor decoration purposes.

4. A massaging mattress, as claimed in claim 3, wherein said array formed by said beads (2) and said magnets (1) can be of such an arrangement so that there are provided three or five wooden beads between each two magnets, making the distance between each two magnets 7-12 centimeters.

5. A massaging mattress, as claimed in claim 2, wherein said ropes (3) can be of nylon, polyamide fibre, waxed cotton thread or silk thread, and said glue (4) are any kind of glue, generally used for indoor decoration purposes.

6. A massaging mattress, as claimed in claim 1, wherein said array formed by said wooden beads (2) and said magnets (1) can be of such an arrangement that there are provided three or five wooden beads between each two magnets, making the distance between each two magnets 7-12 centimeters.

7. A massaging mattress, as claimed in claim 1, wherein said mattress is made into the shape of a pillow having a waved surface, having such an array formed by said beads (2) and said magnets (1) so that there are provided only two wooden beads between each two magnets.

8. A massaging mattress, comprising an elastic stuffing (6) and a compound covering (5), said mattress being provided between said elastic stuffing (6) and said compound covering (5) with an array including wooden beads (2) alternating with magnets said magnets and said beads being interconnected by flexible members so as to form a net (1), each of said wooden beads (2) is like a truncated ellipsoid having two ends forming two parallel circular planes, said beads' maximum circular cross-sectional diameter being disposed proximate their mid-portion and being the same as said beads' height which is a distance between said beads' two ends, and there is provided a through hole penetrating the center of said beads.

9. A massaging mattress, as claimed in claim 8, wherein the maximum circular cross-sectional diameter and the height of said wooden beads (2) are both 16 mm.

10. A massaging mattress, as claimed in claim 8, wherein said beads (2) are made of hard wood.

11. A massaging mattress, as claimed in claim 10, wherein said array formed by said breads (2) and said magnets (1) can be of such an arrangement that there are provided three or five wooden beads between each two magnets, making the distance between each two magnets 7-12 centimeters.

12. A massaging mattress, as claimed in claim 10, wherein said mattress is made into the shape of a pillow having a waved surface, having such an array formed by said beads (2) and said magnets (1) so that there are provided only two wooded beads between each two magnets.

13. A massaging mattress, as claimed in claim 8, wherein each of said magnets (1) is of cylindrical shape, said magnets having a circular cross-sectional diameter the same as said magnets' height, and there is also provided a through hole penetrating the center of said magnets (1).

14. A massaging mattress, as claimed in claim 8, wherein said array formed by said breads (2) and said magnets (1) can be of such an arrangement that there are provided three or five wooden beads between each two magnets, making the distance between each two magnets 7-12 centimeters.

15. A massaging mattress, as claimed in claim 8, wherein said mattress is made into the shape of a pillow having a waved surface, having such an array formed by said beads (2) and said magnets (1) so that there are provided only two wooded beads between each two magnets.

16. A massaging mattress, comprising an elastic stuffing (6) and a compound covering (5), said mattress being provided between said elastic stuffing (6) and said compound covering (5) with an array including wooden beads (2) alternating with magnets (1), each of said magnets (1) is of cylindrical shape, said magnets having a circular cross-sectional diameter the same as said magnets' height, and there is also provided a through hole penetrating the center of said magnets (1).

17. A massaging mattress, as claimed in claim 16, wherein the diameter and height of said magnets (1) are both 16 mm.

18. A massaging mattress, as claimed in claim 16, wherein said magnets (1) are permanent magnets, with a surface field intensity ranging between 500 and 2,000 Gauss.

19. A massaging mattress, as claimed in claim 16, wherein said array formed by said breads (2) and said magnets (1) can be of such an arrangement that there are provided three or five wooden beads between each two magnets, making the distance between each two magnets 7-12 centimeters.

20. A massaging mattress, as claimed in claim 16, wherein said mattress is made into the shape of a pillow having a waved surface, having such an array formed by said beads (2) and said magnets (1) so that there are provided only two wooded beads between each two magnets.

* * * * *

UNITED STATES PATENT AND TRADEMARK OFFICE
CERTIFICATE OF CORRECTION

| | | |
|---|---|---|
| PATENT NO. : | 5,168,588 | Page 1 of 2 |
| DATED : | December 8, 1992 | |
| INVENTOR(S) : | Hoi Chau CHAN | |

It is certified that error appears in the above-identified patent and that said Letters Patent is hereby corrected as shown below:

At column 1, line 37, delete "sore" and insert --store--.

At column 1, line 45, delete "tun" and insert --turn--.

Figure 4B:
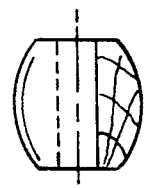
FIG. 4 is a detailed drawing of the wooden bead.
Figure 5B:
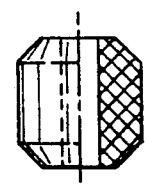
FIG. 5 is a detailed drawing of the magnet.
Figure 4A:
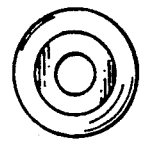
Figure 5A:
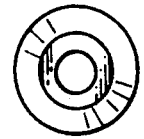

At column 1, line 64, delete "FIG. 4 is detailed drawing of a wooden bead; FIG. 5 is a detailed drawing of the magnet;" and insert
--FIG. 4A is an end view of a wooden bead according to the preferred embodiment of the present invention;
FIG. 4B is a plan view in partial cross-section of the wooden bead depicted in FIG. 4A;
FIG. 5A is an end view of a magnet according to the preferred embodiment of the present invention;
FIG. 5B is a plan view in partial cross-section of the magnet depicted in FIG. 5A; and--

At column 1, line 66, after "is a" insert --cross-sectional--

At column 2, line 14, delete "FIG. 4 shows" and insert --FIGS. 4A and 4B show--.

At column 2, line 25, delete "FIG. 5 shows" and insert --FIGS. 5A and 5B show--.

At column 3, line 21, delete "produces" and insert --products--.

At column 3, claim 3, line 51, delete "can be" and insert --are--.

At column 3, claim 6, line 66, delete "wooden".

UNITED STATES PATENT AND TRADEMARK OFFICE
CERTIFICATE OF CORRECTION

PATENT NO. :   5,168,588

DATED :   December 8, 1992

INVENTOR(S) :   Hoi Chau CHAN

It is certified that error appears in the above-identified patent and that said Letters Patent is hereby corrected as shown below:

At column 4, claim 11, line 30, delete "breads" and insert --beads--.

At column 4, claim 12, line 39, delete "wooded" and insert --wooden--.

At column 4, claim 14, line 48, delete "breads" and insert --beads--.

At column 4, claim 15, line 58, delete "wooded" and insert --wooden--.

At column 5, claim 19, line 9, delete "breads" and insert --beads--.

At column 5, claim 19, line 10, after "arrangement" insert --so--.

At column 6, claim 20, line 8, delete "wooded" and insert --wooden--.

Signed and Sealed this

Twelfth Day of April, 1994

*Attest:*

BRUCE LEHMAN

*Commissioner of Patents and Trademarks*

*Attesting Officer*